(12) United States Patent
Kaneko et al.

(10) Patent No.: US 6,355,232 B1
(45) Date of Patent: *Mar. 12, 2002

(54) AGENT FOR PROTECTING SKIN AND HAIR MOISTURE

(75) Inventors: Teruhisa Kaneko, Tokyo; Tomoya Tanaka, Kanagawa; Masaaki Nagase, Tokyo, all of (JP)

(73) Assignee: Takasago International Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/331,418

(22) PCT Filed: Dec. 16, 1997

(86) PCT No.: PCT/US97/23266

§ 371 Date: Jun. 21, 1999

§ 102(e) Date: Jun. 21, 1999

(87) PCT Pub. No.: WO98/27958

PCT Pub. Date: Jul. 2, 1998

(30) Foreign Application Priority Data

Dec. 20, 1996 (JP) .............................. 8-341107

(51) Int. Cl.[7] .............................. A61K 7/06; A61K 7/00; C07C 233/05
(52) U.S. Cl. .................. 424/70.1; 424/401; 564/203
(58) Field of Search ........................ 554/66; 424/401, 424/70.1; 564/203

(56) References Cited

U.S. PATENT DOCUMENTS

| 5,476,661 A | 12/1995 | Pillai et al. .............. 424/401 |
| 5,525,709 A | 6/1996 | Davey et al. |

FOREIGN PATENT DOCUMENTS

| FR | 2 729 079 | 7/1996 |
| GB | 2 213 723 A | 8/2000 |

OTHER PUBLICATIONS

International Search Report (1999).
European Search Report dated May 23, 2000.

Primary Examiner—Gollamudi S. Kishore
Assistant Examiner—Brian K. Seidleck
(74) Attorney, Agent, or Firm—Sughrue Mion, PLLC

(57) ABSTRACT

A skin protective agent which comprises as a sole ceramide component the erythro (2S, 3R) type of a ceramide and has a remarkably excellent water-barrier ability.

14 Claims, 1 Drawing Sheet

AGENT FOR PROTECTING SKIN AND HAIR MOISTURE

This application is a 371 of PCT/US97/23266, filed Dec. 16, 1997.

FIELD OF THE INVENTION

This invention relates to a skin protective agent which exhibits a water-barrier function to human skin including hair.

BACKGROUND OF THE INVENTION

Skin exposed to severe external environment, together with aging, causes rough skin, which is also referred to as a dry skin. Dry skin, that is, the dryness of skin, is basically brought about by an inability of the skin's normal function of regulating the moisture (water) content of the skin and other protection systems. The main role in these functions comes from water.

It has recently become clear that the water in the skin (stratum corneum) not only performs the moisturization as a simple physicochemical action for skin but also control's the enzymatic activities in the skin metabolic system. There has been reported, for example, the NMF (Natural Moisturizing Factor) generation based on the degradation of filaggrin (Dermatology, 2000, 773 (1993)) or the desquamation of corneocytes due to the digestion of intercellular adhesive factors (intercellular lipids, desmosomes and the like) (Dermatology, 100, 510 (1993)). The reduction in enzyme activities and the imbalance of keratinization as set forth above are caused by an insufficient moisturization of the stratum corneum, that is, the reduction of a water-barrier level. Therefore, it is to be said that the water-barrier abilities are the essential function to maintain the healthy skin. Although the water-barrier function depends upon the skin surface lipids, the amino acids as the NMF, and intercellular lipids of the stratum corneum, etc., it has been clarified that the intercellular lipids contributes highly to the barrier function (J. Inv. Dermatol., 84, 282 (1985)). The intercellular lipids mainly consist of ceramides, fatty acids, cholesterol and cholesterol sulfate (J. Inv. Dermatol., 88, 709 (1987)), and the total and respective levels of these lipids may be influenced by diet, age, race, environment (for example, seasons) and other factors (the 17th IFSCC, 2, 865 (1992)).

To provide a water-barrier property, there has been hitherto suggested the incorporation of various water retention agents into cosmetics.

There has been recently suggested a skin protective agent which comprises a racemate of ceramides, which is a mixture of the erythro and threo types of ceramides (See, Japanese Patent Kokai Nos. 327563/1992 and 165690/1995). Ceramides form the erythro and threotypes based on the conformation of the hydroxy group and the secondary amines and the respective types may take the different steric configurations represented by "S" and "R".

BRIEF SUMMARY OF THE INVENTION

The present inventors have made earnest studies to develop a skin protective agent providing an excellent water barrier benefit, and, as a result, have found that the erythro (2S,3R) type, an optically active species of ceramides, exerts a more remarkable excellent water-barrier function as compared with the recemate. These erythro (2S,3R) ceramides are available through synthetic route of manufacture, as described below.

It is, accordingly, a primary object of this invention to provide a skin protective agent which exhibits a remarkably excellent water-barrier property.

DETAILED DESCRIPTION OF THE INVENTION

Figure 1:
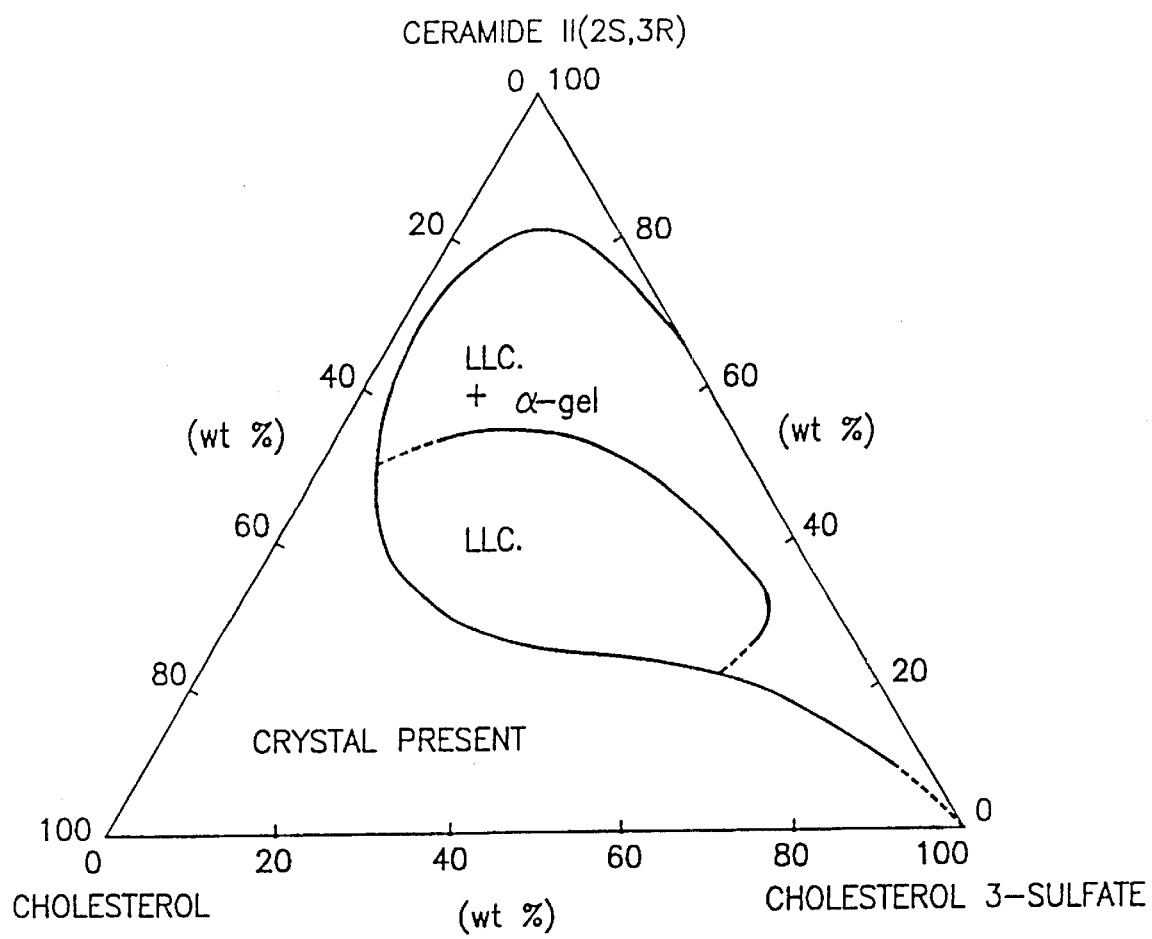
FIG. 1 is a phase diagram of the ceramide-II/cholesterol/cholesterol 3-sulfate system in a phosphate buffer at 40° C.

This invention relates to a skin protective agent which comprises as a substantial sole ceramide component an erythro (2S, 3R) type of a ceramide. The term "sole ceramide component" as used herein means that the said component is not substantially contaminated by other optical isomers and more preferably the said erythro (2S, 3R) type comprises more than 95% of the total ceramide molecules.

The ceramides as referred to herein include ceramides-I, -II, -III, -IV, -V, -VI and -VII and all ceramides are effective, as far as they have the configuration characteristics of this invention, in other words, they are essentially composed of the erythro (2S, 3R) type, and ceramide-II is preferable in view of its effect, ease of its synthesis, etc. This invention will be explained hereafter in regard to the erythro (2S, 3R) type of ceramide II as a representative.

The erythro (2S, 3R) type of ceramide-II has the formula (I)

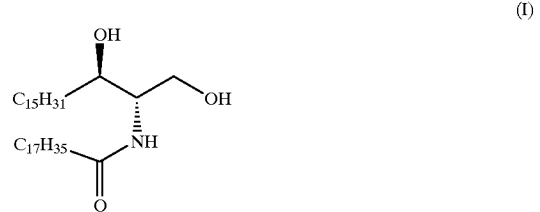

and has a melting point of 106° C.

For reference, the erythro (2R, 3S) type of ceramide-II has the formula (II)

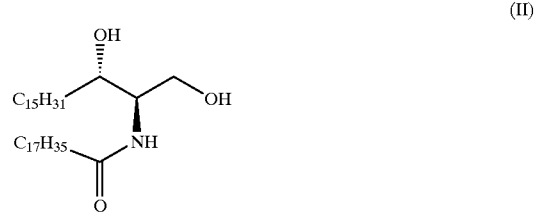

and has a melting point of 112° C.

The threo (2S, 3S) type of ceramide-II has the formula (III)

(III)

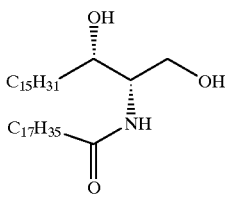

and has a melting point of 101° C.

The threo (2R,3R) type of ceramide-II has the formula (IV)

(IV)

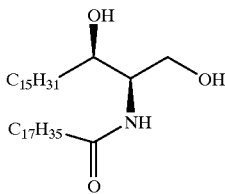

and has a melting point of 100° C.

A racemate of the types of the above formulae (I)/(II)/(III)/(IV)=45/45/5/5 has a melting point of 103° C. and a racemate of the types of the above formulae (I)/(II)/(III)/(IV)=20/20/30/30 has a melting point of 92° C.

The erythro (2S,3R) type of ceramide-II may be preferably prepared according to the process which comprises subjecting a 2-N-acylamino-higher acyl acetic acid ester compound having the formula (V)

(V)

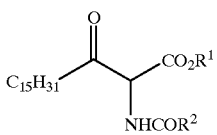

(wherein $R^1$ is an ester residue such as a lower alkyl group and the like, and $R^2$ is a hydrogen atom, a lower alkyl group, a lower alkoxy group and the like) to asymmetric hydrogenation using as a catalyst a ruthenium-optically active phosphinic acid complex to produce an optically active (2R,3S)-2-N-acylamino-3-hydroxyoctadecanoic acid derivative, hydroxy inversion, reducing and hydrolyzing the derivative thus produced to form an optically active (2S,3R)-dihydrosphingosine and when N-acylating the product thus formed with a higher carboxylic acid halide having the formula (VI)

$C_{17}H_{25}$ COX  (VI)

(Wherein X is a halogen atom); thereby producing the erythro (2S,3R) type of ceramide-II with a high optical purity.

The erythro (2S,3R) type thus produced may be used in the same dosage forms as those well-known the prior art skin protecting agents, and may usually be used together with other amphipathic substances.

Examples of the amphipathic substances which may be preferably used in this invention include surface active agents having a HLB-value of not less than 5 to not more than 16, higher alcohols, higher fatty acids, lipids, polar oily substances and the like. More specifically, examples of the surface active agents include acryloyl salts stearoyl sulfates (e.g., sodium salt), stearoyl lactylate, stearoyl isolactiliate etc., as well as those agents of a polyoxyethylene-, polyhydric alcohol ester-, or ethylene oxide-propylene oxide block copolymer-type. Examples of the higher alcohols include lauryl alcohol, myristyl alcohol, cetanol, cetostearyl alcohol, stearyl alcohol, oleyl alcohol, lanolin alcohol, isostearyl alcohol, behenyl alcohol and the like. Examples of the higher fatty acids include lauric acid, myristic acid, palmitic acid, stearic acid, behenoic acid, oleic acid, linolic acid, isostearic acid and the like. Examples of the lipids include cholesterol sulfate, lecithin, phosphatidylserine, phosphatidylglycerol, phosphatidylinositol, sphingomyelin and the like. Examples of the polar oily substances include was esters, olive oil, soybean oil, sunflower oil, ester oils such as ethyl oleate, decyl oleate, or myristyl lactate and the like.

Particularly preferable amphipathic substances may include stearoyl sulfates, catanol, cetosytearyl alcohol, stearyl alcohol, palmitic acid, stearic acid, lectin and the like. A mixing ratio of ceramide/other amphipathic substance of 5/95 by weight is preferable and the ratio of 20/80~80/20 is particularly preferable.

Further, it is also preferable to combine the said mixture with at least one of cholesterol, phytosterol and the like. In this case, a mixing ratio of the said mixture/cholesterol and/or phytosterol by weight may be preferably 95/5~30/70, particularly preferably 95/5~45/55.

The erythro (2S,3R) type of ceramide-II mixed as described above may be, if desired, used as cosmetics in the form of a liposome solution, an emulsion, a water-alcohol solution, an oily solution, or an oil-alcohol solution, a gel, a dispersion, a solid stick, a spray or an aerosol. Examples of these cosmetics include a conditioner, a face lotion, a milky lotion, a cream, a beauty lotion and the like. A amount of the erythro (2S,3R) type of ceramide-II to be mixed for cosmetics may be usually about 0.01 to 20%, preferably 0.05 to 10%, most preferably 0.1 to 5%.

DESCRIPTION OF SPECIFIC EMBODIMENTS

This invention will be more fully illustrated by way of the following examples, but these examples are not to be limiting this invention.

Synthesis of ceramide-II of erythro (2S,3R) type

To a 300 ml-volume stainless autoclave which had been previously replaced with nitrogen was added a solution of 8.4 g (22.7 mmol) of methyl 2-N-acetamido-hexadecanoylacetate and 102 mg (0.057 mmol) of a ruthenium-optically active phosphinic acid complex $Ru_2Cl_4$ [(−)-T-BINAP]$_2$ (NEt$_3$) (wherein T-BINAP represents 2,2'-bis[di(p-tolyl)phosphino]-1,1'-binaphthyl) in 40 ml of methylene chloride and the reaction was allowed to proceed at 50° C. under a hydrogen pressure of 50 atm for 45 hours. The solvent was distilled off from the hydrogenated reaction mixture and the residue was crystallized from a mixed solvent of n-hexane and ethyl acetate (80:1) to afford 8.4 g of a crystalline substance. The crystalline substance thus obtained was purified by a silica gel column chromatography (n-hexane/ethyl acetate=5/1 to 1/4 (volume ratio) to give 8.0 g of methyl (2R,3S)-2-N-acetamido-3-hydroxyoctadecanoate. Yield=95%, Melting Point=95 to 96° C., Optical purity=98% e.e.

To a solution of 7.59 g (22.1 mmol) of methyl (2R,3S)-2-N-acetamido-3-hydroxyoctadecanoate in benzene (200 ml) was added dropwise under ice-cooling 16.5 ml (0.22 mmol) of thionyl chloride over 30 minutes and the resulting mixture was stirred at room temperature for 4 hours. Water (200 ml) was added under ice-cooling and the resulting mixture was stirred at room temperature for 4 hours. After separating an organic layer, an aqueous layer was extracted with diethyl ether (200 ml) and the combined organic layer was distilled under reduced pressure to remove the solvent, thereby affording 8.89 g of a crude inverted product of (2R,3S)-type. The crude (2R,3S) type thus obtained was added to a mixed solution of 5% aqueous hydrochloric acid (100 ml) and 1.4-dioxane (100 ml) and the resulting mixture was heated under reflux while stirring for 4 hours. To the reaction mixture was added under ice-cooling 6N hydrochloric acid (100 ml) and allowed to stand in a cool place for 16 hours to separate out the amine hydrochloride. The resulting crystalline substance was filtered and dried to give 9.82 g of the hydrochloride. To dry tetrahydrofuran (THF) (300 ml) was added 9.82 g of the hydrochloride obtained as above and lithium aluminum hydride (5.04 g, 0.133 mol) was added while stirring under ice-cooling. Then, the resulting mixture was heated under reflux while stirring for 30 minutes. The reaction mixture was treated with 10% aqueous sodium hydroxide (2000 ml) under ice-cooling and extracted with diethyl ether (2000 ml×2). The combined organic layer was washed with saturated aqueous sodium chloride, dried over anhydrous sodium sulfate and the solvent was distilled off under reduced pressure to give 6.45 g. Of dihydrosphingosine.

The dihydrosphingosine thus obtained was N-acylated using an equalmolar amount of octadecanoyl chloride. Thus, ceramide-II of erythro (2S,3R) type was prepared of an optical density of not less than 99%. The erythro (2S,3R) type was compared with other optically active isomers and racemates and the so-called pseudoceramides in regard to aptitude for a skin protective agent.

Evaluation Tests and Results

1. Solubility in cosmetic solvents

Solubilities of ceramide-II (hereinafter referred to as CeII) of (2S,3R) type and ceramides of other optical isomers were studied. Ethanol, isopreneglycol, propylenglycol, glycerol, oleic acid, ethyl oleate and isopropyl myristate were used as the cosmetic solvents. Each sample was heated up to about 90° C. with vigorous shaking and cooled down to room temperature and then observed visually. The results are shown in the following Table. 1.

TABLE 1

| | erythro | | | | threo | | | | |
|---|---|---|---|---|---|---|---|---|---|
| | (2S,3R) | | (2R,3S) | | (2S,3S) | | | (2R,3S) | |
| | 0.1 | 0.5 | 0.1 | 0.5 | 0.1 | 0.5 | 1 | 0.1 | 0.5 | 1 |
| Ethanol | ○ | X | ○ | X | ○ | X | X | ○ | X | X |
| Isopreneglycol | X | X | X | X | X | X | X | X | X | X |
| Propyleneglycol | X | X | X | X | X | X | X | X | X | X |
| Glycerol | X | X | X | X | X | X | X | X | X | X |
| Oleic acid-90 | X | X | ○ | X | ○ | ○ | X | ○ | ○ | X |
| Ethyl oleate-90 | X | X | X | X | X | X | X | X | X | X |
| Isopropyl myristate | X | X | X | X | X | X | X | X | X | X |

Note:
○: soluble
X: insoluble

Although the solvents used have a relatively high solvency, the (2S,3R) has the lowest solubility and is dissolved in ethanol only at a 0.1% level. Other Ce II's have a relatively high solubility in oleic acid. However, all types have, generally speaking, an extremely low solubility. The results show that the ceramide has a strong molecular force, which is believed to originate in the amide bond as the hydrophilic part and the double long alkyl chains as the hydrophobic part. And, it seems that the extremely low solubility may contribute to a high water-barrier function in the stratum corneum. On the other hand, in order to penetrate Ce II into a rough skin or hair, evaluate the skin care efficacy of Ce II, and design a formulation with Ce II, it is essential to reduce the intermolecular force of Ce II and take the form which may be at least dispersed in cosmetic solvents. In fact, ceramides coexist with other lipids such as a fatty acid, cholesterol (CL) or cholesterol sulfate (CS) and form the lamellar structure in the stratum corneum [Int.J.Dermatol., 20,p.1(1981)].

2. Phase diagram

The phase diagram of the (2S,3R)/CL/CS system in a phosphate buffer (pH 6.86) at a system/buffer weight ratio of 1/1 (40° C.) was prepared. A mixture of CeII, CL and CS was obtained by allowing to stand at 135° C. for 10 minutes. This heating process was repeated twice. To each mixture was added the prescribed buffer and was allowed to stand at 135° C. for 5 minutes to give a uniform mixture. The sample was frozen to −20° C., and then annealed from −20° C. to room temperature to form a more uniform sample mixture. Each sample was observed visually, by a polarization microscope with heat stage and by determination of DSC. It was confirmed by HPLC that decomposition of each component could hardly be brought about due to the heating and mixing process.

The effect of the incorporation of other stratum corneum lipids into the (2S,3R) type was studied to obtain the lamellar liquid crystalline (LLC) phase. Cholesterol sulfate (CS) was chosen because of its strong polar groups. FIG. 1 is the phase diagram of the Ce II/CL/CS/phosphate buffer system. As seen from this Figure, the system of Ce II and CS forms the α-gel structure. This α-gel phase has a solid state in its alkyl chain part, but may take up a large amount of water because of the strong polar group in Cs. It is believed that the incorporation of CL into the α-gel phase makes loose the packing in the alkyl chain part, which results in the formation of LLC. Consequently, Ce II may be dispersed in a cosmetic solvent by making the use of the LLC phase formed the Ce II/CL/CS system and it would be possible to study the effects thereof. In connection with the LLC phase formed as above, the combination of other amphipathic substance such as stearoyl sulfate, lecithin, palmitic acid, etc. with Ce II may basically form the corresponding LLC phase although its range may be larger or smaller.

3. Sample preparation for determination of water-holding capacity (WHC) and water-barrier function (WBF)

A sample solution was prepared, based upon the lamellar liquid crystal (LLC) method of various methods for preparing liposome [Colloids and Surfaces, 69, p.125 (1992)]. Appropriate amounts of the lipid mixture (for example, Ce II (2S,3R)/CL/CS, a weight ratio of 40/30/30, corresponding to the LLC region of the phase diagram) were weighed into a test tube, allowed to stand at 135° C. for 10 minutes, cooled down to room temperature and then appropriate amounts of propylene glycol/glycerol (a weight ration of 1/1) were added to the mixture. These samples were left at 135° C. for 10 minutes and then shaken vigorously. This procedure was repeated three times. Then, oleic acid and an aqueous solution of L-arginine were added in turn and shaken (80 to 90° C.). The LLC gel thus obtained was diluted with a buffer of pH 6.86 to give a vesicle solution of a uniform mixture of ceramides.

4. Tests on water-holding capacity (WHC) and water-barrier function (WBP)

(a) WHC test

A sample solution was applied to a small petri dish and left at 37° C. and a humidity of 40%. The water evaporated as the time lapsed was measured and the ratio of the water remaining in the sample was calculated from the measured value to study WHC. The results are shown in Tables 2 and 3.

The samples tested as shown in Table 2 were all mixtures of ceramide/CL/CS (40/30/30) and dispersed with 10% arginine oleate. A control was an aqueous solution of propyleneglycol/glycerol (1/1).

TABLE 2

| | Water-holding capacity (%) (After 5 hours) |
|---|---|
| (2S,3R) | 22.4 |
| Sp-Ce | 12.2 |
| Quest-Ce | 16.7 |
| Racemate-1 | 11.5 |
| Racemate-2 | 17.2 |
| Control | 0 |

The samples tested as shown in Table 3 were mixtures of (2S,3R)/CL/CS and of (2S,3R)/CL/SSS (=sodium stearylsulfate) (the respective ratios of 40/30/30) and dispersed with lot arginine oleate. It was shown that a better result could be obtained by using sodium stearylsulfate.

TABLE 3

| | Water-holding capacity (%) (After 5 hours) |
|---|---|
| (2S,3R)/CL/CS | 22.4 |
| (2S,3R)/CL/SSS | 41.7 |

(b) WBr test

A sample solution was coated over a supporting membrane covered with a protein at the surface and left under vacuum overnight to remove water thoroughly. The membrane was fixed in the stainless dish containing 20 ml of water and allowed to stand at 37° C. and a humidity of 40%. The evaporated water was calculated per time unit and area unit to determine the water-evaporation rate of WBF. Comparative results of ceramides are shown in Tables 4 and 5.

All samples tested as shown in Table 4 were mixtures of ceramide/CL/CS (40/30/30) and dispersed with 10% arginine oleate.

TABLE 4

| | Water-evaporation rate (mg/hr/cm2) |
|---|---|
| (2S,3R) | 2.5 |
| Racemate-1 | 5.4 |
| SP-Ce | 4.6 |
| Non-treated | 6.7 |

All samples tested as shown in Table 5 were mixtures of ceramide/CL/CS (40/30/30) and dispersed with 10% arginine oleate.

TABLE 5

| | Water-evaporation rate (mg/hr/cm2) |
|---|---|
| (2S,3R) | 2.5 |
| (2R,3S) | 2.9 |
| (2S,3S) | 3.6 |

It can be seen from the above results that the (2S,3R) type has a significantly higher water-holding capacity than the racemates, the SP ceramide (available from Kao Corporation; a pseudoceramide), etc. It is believed that this difference may originate in the packing state of each LLC structure. In other words, the LLC structure based upon the (2S,3R) type is considered to be more rigid than other types. As shown in Tables, the capacity of the (2S,3R) type to restrain the water evaporation is also more superior to other types. This is believed that other Ce II's may be mixed with the stratum corneum lipids to naturally form a racemate-like structure, and, consequently, WBF of other types may be reduced as compared with the (2S,3R) type.

Accordingly, the (2S,3R) type has a higher capacity of WBF as compared with other types of ceramides. In view of the above, it is believes that the (2S,3R) type has less influence upon the packing state of the intercellular structure in the stratum corneum and is very much effective in recovering the normal skin-barrier capacity.

6. Transepidermal water-loss (TEWL) test

The forearm was treated with chloroform/methanol (1/1), each sample was coated on the site and TEWL was determined (n=4, twice per day, used for 2 days). The data obtained after 10 hours are shown in Table 6.

All tested samples were the (2S,3R) type and the (2S,3S) type and were mixtures of ceramide/CL/SSL (=sodium stearyllactate) (50/20/30). They were dispersed with 10% arginine oleate.

TABLE 6

| | TEWL (g/m$^2$/hr) |
|---|---|
| Non-treated | 2.3 |
| Treated (Damaged skin) | 5.9 |
| (2S,3R) | 2.8 |
| (2S,3S) | 4.1 |

It can be seen that ceramides of both types can significantly improve TEW as compared with the uncoated sites, but the (2S,3R) type can recover to the TEWL value of the non-treated normal skin more rapidly. This correlates well with the in vitro WBF results.

7. Test on conditioner effect to hair (WHC)

Hairs were treated with chloroform/methanol (2/1) and bundles of hairs were coated with samples, rinsed away and then dried under vacuum overnight. They were left at 35° C. and a humidity of 70% overnight. They were weighed to determine the hydrated amount to the dried hairs as WHC. The results are shown in Table 7.

All tested samples were the (2S,3R) type and the (2S,3S) type and were mixtures of ceramide/CL/SA (=stearic acid) (40/20/40). They were dispersed with 10% arginine oleate.

TABLE 7

|  | Water-holding capacity (%) |
| --- | --- |
| Normal hair | 8.3 |
| Damaged hair | 3.3 |
| (2S,3R) | 8.2 |
| Racemate-2 | 7.3 |

It can be seen that the recovery to normal hair can be promoted more rapidly by treating with the (2S,3R) type.

What is claimed is:

1. A protective agent for skin or hair which comprises as a substantial sole ceramide component an erythro (2S, 3R) ceramide, where the erythro (2S, 3R) ceramide has the chemical structure:

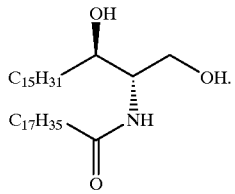

2. The protective agent as claimed in claim 1 wherein said erythro (2S, 3R) type comprises more than 95 mole % of the total ceramide molecules.

3. The protective agent as claimed in claim 1 further comprising an amphiphatic substance.

4. The protective agent as claimed in claim 3 wherein a weight ratio of said ceramide to said amphiphatic substance is in the range of from 5:95 to 95:5.

5. The protective agent as claimed in claim 3 wherein a weight ratio of said ceramide to said amphiphatic substance is in the range of from 20:80 to 80:20.

6. The protective agent as claimed in claim 3 wherein said amphiphatic substance is a substance selected from the group consisting of a surface active agent, a higher alcohol, a fatty acid, a lipid, and a polar oily substance, said amphiphatic substance having a HLB-value of from not less than 5 to not more than 16.

7. The protective agent as claimed in claim 3 wherein it further comprises cholesterol or phytosterol.

8. The protective agent as claimed in claim 4 wherein the weight ratio of the mixture of the ceramide with the amphiphatic substance to cholesterol or phytosterol is in the range of from 95:5 to 30:70.

9. A composition comprising the protective agent of claim 1 and a cosmetically or pharmaceutically acceptable vehicle therefore.

10. The composition as claimed in claim 9 wherein it is a cosmetic for treating skin or hair.

11. The composition of claim 9 wherein the protective agent is in an amount of from about 0.01 to about 20%.

12. A method for treating skin or hair comprising: applying an erythro (2S, 3R) ceramide as the substantial sole ceramide component to the surface of an epidermal derivative selected from the group consisting of skin and hair, where the erythro (2S, 3R) ceramide has the chemical structure:

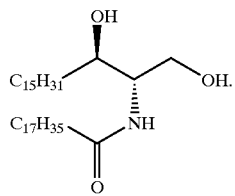

13. The method of claim 12 wherein the erythro (2S, 3R) ceramide is applied in combination with a vehicle therefore and the amount of the erythro (2S, 3R) ceramide is from 0.01% to about 20%.

14. The protective agent of claim 1, where the ceramide in the protective agent comprises more than 95% erythro (2S, 3R) ceramide.

* * * * *